US012636023B2

(12) United States Patent
Mehrabi

(10) Patent No.: US 12,636,023 B2
(45) Date of Patent: May 26, 2026

(54) CROSSING CATHETER SYSTEM FOR CROSSING CHRONIC TOTAL OCCLUSION AND A METHOD FOR OPERATING THE CROSSING CATHETER SYSTEM

(71) Applicant: BIOTRONIK AG, Buelach (CH)

(72) Inventor: Azadeh Mehrabi, Meilen (CH)

(73) Assignee: BIOTRONIK AG, Buelach (CH)

( * ) Notice: Subject to any disclaimer, the term of this patent is extended or adjusted under 35 U.S.C. 154(b) by 143 days.

(21) Appl. No.: 18/579,719

(22) PCT Filed: Aug. 9, 2022

(86) PCT No.: PCT/EP2022/072290
§ 371 (c)(1),
(2) Date: Jan. 16, 2024

(87) PCT Pub. No.: WO2023/017006
PCT Pub. Date: Feb. 16, 2023

(65) Prior Publication Data
US 2024/0341781 A1 Oct. 17, 2024

(30) Foreign Application Priority Data

Aug. 10, 2021  (EP) ..................................... 21190662
Jan. 27, 2022  (EP) ..................................... 22153662

(51) Int. Cl.
*A61B 17/3207* (2006.01)
*A61B 17/00* (2006.01)
(Continued)

(52) U.S. Cl.
CPC ........ *A61B 17/22* (2013.01); *A61B 17/00234* (2013.01); *A61B 17/320758* (2013.01);
(Continued)

(58) Field of Classification Search
CPC ............ A61B 17/22; A61B 17/320758; A61B 17/320725; A61B 17/32075; A61B 17/320783; A61M 25/0054
See application file for complete search history.

(56) References Cited

U.S. PATENT DOCUMENTS

| | | | | |
|---|---|---|---|---|
| 5,047,040 A | * | 9/1991 | Simpson | ............ A61B 17/3207 606/159 |
| 5,423,846 A | | 6/1995 | Fischell | |

(Continued)

FOREIGN PATENT DOCUMENTS

CN          211675820 U          10/2020

OTHER PUBLICATIONS

European Search Report from the corresponding European Patent Application No. EP 22153662.6, dated Jun. 28, 2022.
(Continued)

*Primary Examiner* — Tuan V Nguyen
(74) *Attorney, Agent, or Firm* — Greer, Burns & Crain, Ltd.; Steven P. Fallon

(57) ABSTRACT

A crossing catheter system for crossing chronic total occlusion includes or consists of a support catheter having a support catheter shaft defining a support catheter lumen capable of receiving a dilator. A dilator is arranged within the support catheter lumen. A locking handle is arranged at a proximal support catheter end. The dilator has a proximal segment with a uniform radial circumference and a distal segment that has a radial circumference that is smaller than the radial circumference of the proximal segment.

21 Claims, 7 Drawing Sheets

(51) Int. Cl.
    *A61B 17/22*          (2006.01)
    *A61B 90/00*          (2016.01)
(52) U.S. Cl.
    CPC .... *A61B 90/39* (2016.02); *A61B 2017/00238*
        (2013.01); *A61B 2017/00305* (2013.01); *A61B*
            *2017/00477* (2013.01); *A61B 2017/00831*
        (2013.01); *A61B 2017/22038* (2013.01); *A61B*
            *2017/22094* (2013.01); *A61B 2090/3966*
                (2016.02); *A61B 2217/007* (2013.01)

(56)                    References Cited

U.S. PATENT DOCUMENTS

| 6,228,052 | B1 * | 5/2001 | Pohndorf | .......... | A61M 25/0017 |
|---|---|---|---|---|---|
| | | | | | 604/93.01 |
| 2005/0149096 | A1 | 7/2005 | Hilal et al. | | |
| 2006/0253145 | A1 * | 11/2006 | Lucas | .................... | A61B 17/22 |
| | | | | | 606/159 |
| 2017/0136212 | A1 | 5/2017 | Garrison et al. | | |
| 2021/0001096 | A1 | 1/2021 | Gianotti et al. | | |

OTHER PUBLICATIONS

International Search Report from the corresponding International
Patent Application No. PCT/EP2022/072290, dated Nov. 3, 2022.
European Office Action from the corresponding European Patent
Application No. 22764385.5, dated Aug. 6, 2025.

* cited by examiner

CROSSING CATHETER SYSTEM FOR CROSSING CHRONIC TOTAL OCCLUSION AND A METHOD FOR OPERATING THE CROSSING CATHETER SYSTEM

PRIORITY CLAIM

This application is a 35 U.S.C. 371 US National Phase and claims priority under 35 U.S.C. § 119, 35 U.S.C. 365 (b) and all applicable statutes and treaties from prior PCT Application PCT/EP2022/072289, which was filed Aug. 9, 2022, which application claimed priority from EP Application 21190662.3, which was filed Aug. 10, 2021, and from EP Application 22153662.6, which was filed Jan. 27, 2022.

FIELD OF THE INVENTION

The present invention concerns a crossing catheter system for crossing a chronic total occlusion.

BACKGROUND

A chronic total occlusion (CTO) is the complete obstruction of a coronary artery. CTO having soft CTO caps in the beginning can start aging and can get hard, fibrous CTO caps with time. In the traditional approach for treating a CTO a physician uses a selected guidewire which is inserted via a support catheter. First the physician uses a soft guidewire to maneuver to the CTO. If the physician realizes that the CTO is already too hard to cross with the soft guidewire, he must pull out the soft guidewire completely out of the support catheter and must use a guidewire having more stiffness. However, a hard, fibrous CTO cap makes a penetration of the CTO with a guidewire more difficult or, in some cases, impossible. Thus, attempts to cross these lesions with a guidewire can result in the inability to penetrate the proximal CTO cap and the distal CTO cap or crossing the CTO. Further problems associated with guidewires are slippage and buckling, the deflection of the guidewire into the subintimal space. Sometimes the guidewire passes through the CTO, but delivery of subsequent devices is not possible as the penetration point is too small.

There are varieties of specialized CTO guidewires available in the market to overcome some of the above stated the challenges. Nevertheless, the physicians need to select a proper guidewire which is able to cross the CTO based on the lesion morphology during the course of treatment therefore they need to repeatedly change from one guidewire to another guidewire, for example using a guidewire with more tip gram load or a guidewire with tip stiffness. Moreover, the lack of the precise guidewire control to feel the manipulation of device in situ for preventing guidewire to flex and kink or perforate the vessel is not possible. In addition to that, the inability of physicians to see the course of vessel while the guidewire at the site of occlusion stills remains a challenge. This could significantly increase the procedure time hence increasing the use of catheter laboratory resources.

Specialized CTO crossing devices, such as ultrasound-guided vibration angioplasty, blunt microdissection catheters, and reentry catheters have been developed to facilitate the introduction and placement of the guidewire into distal arteries. Nevertheless, despite the excellent evidence, these devices are not used in routine clinical practice. Such devices can be very cost prohibitive, making doctors reluctant to pull them off the shelf early in a procedure. In addition, these devices may employ complicated actions that require a learning curve in a situation in which user experience is critical.

EP 3 322 470 B1 discloses a functionally integratable catheter system CTO dilator which needs to have a specific tip called "CTO Penetration Tip" to only penetrate the CTO lesion proximal cap with the dilator. In order to cross the CTO a guidewire is used. However, as it stated before it is not always possible to cross a CTO with a guidewire, specifically not older occlusions with a greater CTO length and highly calcified CTO caps. The suggested dilator tips are designed for a reentry technique which avoids crossing the CTO and are not suitable for an intraluminal technique which is going through the CTO.

EP 2 473 122 B1 discloses a blade which has a beveled tip creating a channel to help penetrate the CTO. Attached to the proximal part of the blade is a handle which has a spring element. It advances a sharpened tip of the blade axially and helps to move the blade axially and rotationally relative to the microcatheter. With this system the physicians is not able to see the course of vessel while the blade is at the site of occlusion.

SUMMARY OF THE INVENTION

A crossing catheter system for crossing a chronic total occlusion includes a support catheter defining a lumen configured to receive a dilator. The support catheter has a distal support catheter end, a proximal support catheter end and a support catheter shaft extending between the support catheter distal end and the support catheter proximal end. A dilator is at least partially arranged within the lumen. The dilator includes a distal dilator end, a proximal dilator end, and a dilator shaft extending between the distal dilator end and the proximal dilator end. The distal dilator end is connected or connectable to the dilator shaft. The distal dilator end includes a proximal and a distal segment. The proximal segment is configured to be connectable to the dilator shaft. The proximal segment has a uniform radial circumference. The radial circumference of the distal segment is smaller than the radial circumference of the proximal segment. A locking handle is configured to lock the dilator in a defined position within the lumen. The locking handle is arranged at the proximal support catheter end or the support catheter shaft.

BRIEF DESCRIPTION OF THE DRAWINGS

Features and advantages of the present invention and embodiments thereof shall be explained in the following figures, wherein.

DETAILED DESCRIPTION OF THE PREFERRED EMBODIMENTS

Figure 1:
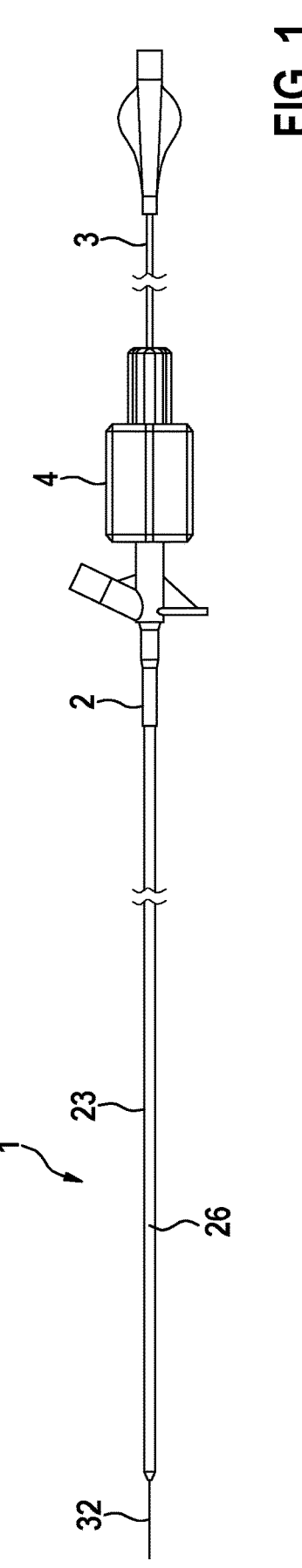
FIG. 1 shows an embodiment of a crossing catheter system.

A preferred crossing catheter system for crossing a chronic total occlusion generally includes or consists of a support catheter, a dilator catheter (hereinafter shortly named dilator), a locking handle, and optionally at least one manifold. The support catheter includes a distal support catheter end, a proximal support catheter end and a support catheter shaft extending between the support catheter distal end and the support catheter proximal end. The support catheter shaft defines a support catheter lumen capable of receiving a dilator. A dilator includes a distal dilator end, a proximal dilator end and a dilator shaft extending between the distal dilator end and the proximal dilator end. The dilator is at least partially arranged within the support catheter lumen of the support catheter. The distal dilator end has a proximal segment, a distal segment, and optionally one or more intermediate segments being arranged between the proximal segment and the distal segment. The proximal segment is connected to the dilator shaft. The proximal segment has a uniform radial circumference, and wherein the radial circumference of the distal segment is smaller than the radial circumference of the proximal segment. A locking handle for locking the dilator in a defined position is within the support catheter shaft. The locking handle is arranged at the proximal support catheter end or the support catheter shaft.

This crossing catheter system enables a crossing of an occlusion or of a CTO having soft CTO caps using only the dilator for crossing but also enables a crossing of hard, fibrous CTO caps using the support catheter together with the dilator for crossing the CTO. The support catheter works in tandem with the dilator catheter and the locking handle, providing additional column strength and increasing the "pushability" of the crossing catheter system to move through the CTO.

The support catheter has a distal support catheter end, a proximal support catheter end and a support catheter shaft extending between the support catheter distal end and the support catheter proximal end. The distal support catheter end is the end which is intended to be inserted into a human or animal body. The proximal outer catheter end is the end, which is intended to be operated by an operator, in particular a physician.

The proximal support catheter end includes a locking handle or may be connected to the locking handle. The locking handle includes a locking mechanism for locking the dilator in a defined position. Thus, the locking handle locks the dilator and prevents the dilator from moving. Therefore, the whole catheter, namely the dilator together with the support catheter can be pushed through the CTO. Thus, a locking of the dilator within the support catheter by using the locking handle enables a higher column strength and thus a higher pushability. Pushability refers to a force applied by a physician to advance the catheter towards the CTO. Clearly spoken pushability refers to a force the distal dilator end experiences when a force is being applied to the proximal support catheter end and/or to the locking handle.

The locking handle also makes it easier for an operator, e.g. a physician, to operate the crossing catheter system and to push the dilator or crossing catheter system. The locking handle may be a pushing handle enabling a pushing by an operator and a locking handle of the dilator in defined position. The locking handle may include visual or haptic markings. The locking handle may have a gripping surface. A gripping surface could help the operator to control the catheter. The locking handle may have an ergonomic design to make it easier for the operator to grip the crossing catheter system during the operation. The locking handle may be configured to simultaneously be attached to the support catheter and the dilator.

The support catheter may include a manifold which is connected to the locking handle.

The support catheter may include one or more support catheter ports, preferably one or more ports for a fluid medium, e.g. a flushing port, an inflation and/or deflation port. The distal support catheter end is the end which is inserted into a human or animal body. The proximal outer catheter end is the end, which is operated by an operator, in particular a physician.

The support catheter and/or the locking handle may include a hemostatic valve (also referred to as hemostasis valve) for sealing purposes. In one embodiment the locking element can include the hemostatic valve for sealing and locking purposes. A hemostasis valve has a seal, which can be locked or unlocked, for example each time the dilator or another device like a balloon catheter, a stent or a needle, is introduced or extracted.

The support catheter may be a reinforced support catheter or may be made of a reinforced material. Preferably, the support catheter shaft and/or the distal support catheter end may be made of a reinforced material. A reinforcement of the support catheter or the support catheter shaft and/or the distal support catheter end enables a better pushability.

The distal support catheter end may be a straight-edged or tubular shaped distal support catheter end. A straight-edged or tubular shaped distal support catheter end improves the pushability and avoids flaring. The support catheter may have a round distal support catheter end. The distal support catheter end may have rounded edges and/or is blunt.

The support catheter distal end can be made from a different material like metal or combination of metal or polymer or polymer with metal infused in it or different materials with (two) different stiffness. The distal support catheter end may have a higher stiffness than stiffer than the support catheter shaft.

The distal support catheter end may include a radiopaque material or radiopaque marker. The distal support catheter end may be made of a (suitable) metal. Preferably, the distal support catheter end includes a metal ring or a metal cap having an opening enabling the dilator tip to fit through the opening. The metal cap or the metal ring enables a reinforcement of the distal support catheter end, while at the same time being radiopaque.

In one embodiment the distal support catheter end may be a straight-edged, round and reinforced distal support catheter end, preferably made of a (suitable) metal or having a metal ring. A reinforced distal support catheter end (e.g. having a metal ring) enables to withstand positive and negative pressure exerted on the crossing catheter system.

A (medical) dilator (also called dilating catheter, dilator catheter or vessel dilator) for insertion in a vascular or cardiovascular system is disclosed. A dilator within the meaning of the invention does not encompass expanding functionalities like a balloon catheter.

The dilator has a distal dilator end, a proximal dilator end and a dilator shaft extending between the distal dilator end and the proximal dilator end. The distal dilator end is the end of the dilator which is intended to be inserted into a human or animal body. The proximal dilator end is the end of the dilator, which is intended to be operated by an operator, in particular a physician. The distal dilator end has at least three different segments (being connected to one another). The distal dilator end has a proximal segment, a distal segment and one or more intermediate segments being arranged between the proximal segment and the distal segment. The proximal segment is connected to the (one or more) intermediate segment(s) and the (one or more) intermediate segment(s) is connected to the distal segment. The distal segment is the segment of the distal dilator end which is intended to (first) cross the CTO. The proximal segment is the segment of the distal dilator end, which is connected to the dilator shaft. In one embodiment the proximal segment, the distal segment and the intermediate segments may be integrally formed with the dilator shaft. In another embodiment the distal dilator end is (releasably) connectable to the dilator shaft. For example, the proximal segment, the distal segment and/or the intermediate segments may be replaceable by other respective segments. This enables the operator to individually adapt the distal dilator end to the specific requirements needed during an operation.

The diameter of the proximal segment is larger than the diameter of the distal segment. The diameter of the proximal segment is larger than the diameter of the one intermediate segment or each of the diameters of the more than one intermediate segments. The diameter of the distal segment is smaller than the diameter of the one intermediate segment or each of the diameters of the more than one intermediate segments. The diameter of the proximal segment is smaller than the diameter of the distal support catheter end. The diameter of the proximal segment may have the same diameter than the diameter of the dilator shaft.

The diameter of the one or more intermediate segments may gradually or progressively or non-constantly decrease from the proximal segment to the distal segment. The diameter of the one or more intermediate segments may decrease from the proximal segment to the distal segment but does not decrease steadily or constantly.

The radial circumference of the proximal segment is larger than the radial circumference of the distal segment. The radial circumference of the proximal segment is larger than the radial circumference of the one intermediate segment or each of the radial circumferences of the more than one intermediate segments. The radial circumference of the distal segment is smaller than the radial circumference of the one intermediate segment or each of the radial circumferences of the more than one intermediate segments. The radial circumference of the proximal segment is smaller than the radial circumference of the distal support catheter end. The radial circumference of the proximal segment is slightly smaller than the radial circumference of the support catheter lumen. The radial circumference of the proximal segment may have the same radial circumference than the radial circumference of the dilator shaft.

The radial circumference of the one or more intermediate segments may gradually or progressively or non-constantly decrease from the proximal segment to the distal segment. The radial circumference of the one or more intermediate segments may decrease from the proximal segment to the distal segment but does not decrease steadily or constantly.

The defined position in which the dilator is lockable within the support catheter shaft may be either a position wherein at least the proximal segment, preferably the proximal, the one or more intermediate segments and the distal segment of the distal dilator end, is situated in the support catheter lumen (e.g. in case of hard CTO caps) or a position wherein the proximal segment (as well as the one or more intermediate segments and the distal segment) of the distal dilator end is not situated in the support catheter lumen (e.g. in case of soft CTO caps).

In one embodiment the one or more intermediate segments may have a thread (similar to a thread of screw). Thus, the intermediate segment may be cone-shaped or frustoconical-shaped having a conical spiral on the external surface of the cone or the frustum of the cone. The pitch of the thread can vary along the one (or more) segment. An intermediate segment having a thread might facilitate the crossing of the CTO.

Preferably, the distal dilator end has only one intermediate segment being a tapered thread, preferably having blunt flanks, and the distal segment having a smaller radial circumference than the proximal segment.

The distal segment can be a sharp or a blunt tip, preferably the distal segment is sharp or has sharp edges (so that is capable to cross a hard stenosis or CTO).

The distal dilator end may be made of a reinforced polymer (e.g. a fiber reinforced polymer), a ceramic, a metal or, an alloy or a combination thereof improving CTO penetration capability. Therefore, the distal dilator end can withstand the pressure applied by the operator. The distal dilator end, preferably the distal segment may be hardened or reinforced. Also the dilator shaft and/or the support catheter shaft and/or the distal support catheter end may be hardened or reinforced. A reinforced crossing catheter system has improved pushability, thus it can be preferably used for intraluminal crossing of a complete CTO.

The stiffness of the distal segment, the proximal segment and the one or more intermediate segments may be different from each other. Preferably, the distal segment has a higher stiffness than the proximal segment and the one or more intermediate segments.

The dilator shaft may have different shaft regions. The different shaft regions may have a different stiffness along a defined length of the dilator shaft. Preferably, the distal support catheter end has a higher stiffness than the proximal support catheter end and the support catheter shaft.

The proximal dilator end may include a dilator manifold.

In one embodiment the dilator may be solid.

In another embodiment the dilator may include one or more dilator lumens. Preferably, the dilator includes two lumens (a first lumen for receiving a guidewire and a second lumen for receiving a fluid medium). The two lumens could run parallel through the dilator. However, the dilator may have only one lumen enabling at the same time injection of a guidewire and a contrast agent. The dilator, preferably the dilator manifold can include a dilator port for injecting fluid medium (e.g. a contrast agent) into at least one of the dilator lumens.

In another embodiment the dilator shaft may be solid and one or two lumens may run parallel to the solid dilator shaft.

A preferred method of operating an aforementioned crossing catheter system includes the steps of inserting the dilator into the support catheter lumen of the support catheter, and optionally retracting at least the proximal part of the distal dilator end into the distal support catheter end, and locking the dilator in a defined position within the support catheter lumen with the locking handle, wherein in the defined position at least the proximal segment of the distal dilator end is situated in the support catheter lumen or the distal dilator end is not is situated in the support catheter lumen, optionally injecting a contrast agent into at least one of the one or more dilator lumens.

Furthermore, a method of treating a chronic total occlusion using the aforementioned crossing catheter system is described.

A method of treating a chronic total occlusion, preferably using an aforementioned crossing catheter system, includes the following steps inserting a dilator having a distal dilator end through the lumen of a support catheter in the vicinity of a CTO, optionally retracting the dilator in a defined position into the support catheter lumen, locking the dilator in a defined position within the support catheter with a locking handle, and crossing the CTO with the crossing catheter system.

In the defined position at least the proximal segment of the distal dilator end is situated in the support catheter lumen or the distal dilator end is not is situated in the support catheter lumen.

The method may further include a step of dotting the (proximal) CTO cap with the distal dilator end to test the status of CTO cap. For crossing soft CTO caps, the dilator alone, in particular the distal segment of the distal dilator end is used. If the operator realizes in the step of dotting that the crossing of the CTO with the dilator, in particular with the distal segment of the distal dilator, alone is not possible, the operator can retract the dilator into the support catheter lumen, in particular in such a way that the distal segment of the distal dilator is arranged in the distal support catheter end, and then lock the dilator using the locking handle, and cross the CTO with distal support catheter end having the distal dilator end arranged therein. Especially for crossing hard CTO caps the support catheter together with the dilator is used. The crossing catheter system according to the invention enables a crossing of different CTO cap hardness.

The proximal segment of the distal catheter end may be kept inside the support catheter, in particular the proximal support catheter end, during the whole operation procedure, preferably in the event of hard CTO caps.

The dilator can be locked in a defined position with the locking handle. Locking the dilator means to lock the dilator shaft with respect to the support catheter to increase the steerability of the crossing catheter system.

After locking the dilator, the operator (e.g. physician) could use the locking handle to penetrate, push, rotate or advance the crossing catheter system across the CTO.

After crossing the CTO the dilator could be retracted completely out of the support catheter lumen while the support catheter remains in the vessel for inserting subsequent devices for example a balloon catheter, a stent, a needle, etc. for further treatment. Subsequent, at least one device, like a balloon catheter, a stent, a needle, etc. may be inserted through the support catheter lumen into the human or animal body. The support catheter and the dilator are adapted to remain together within the patient throughout the operation.

If the operator wants to see the location of the crossing catheter system in the vessel, the locking handle could be unlocked, the contrast medium can be delivered via the flushing port of the dilator into a dilator lumen. If necessary, the operator can make necessary adjustments and continue the procedure.

The crossing catheter system according to the invention as well as the method of CTO treatment gives flexibility to the operator (e.g. the doctor) to choose to cross the CTO without the need to exchange different guidewires with different tip grams as the propose crossing catheter system offers sufficient pushability. The operator is able to see using the contrast agent where the crossing catheter system is located in the CTO. The operator is also able to feel via the friction between the proximal dilator tip and distal support catheter whether or not the distal dilator end is situated in the proximal support catheter end.

A further method of treating a chronic total occlusion, preferably using an aforementioned crossing catheter system, is describe including the following steps inserting a dilator having a distal dilator end through the lumen of a support catheter in the vicinity of a CTO, and choosing either to cross the CTO with the distal segment of the distal dilator end which extends out of the distal support catheter end or to cross the CTO with the distal support catheter end having the distal dilator end arranged within the lumen of the distal support catheter end (wherein the dilator is locked in this position via the locking handle).

Although the support catheter, the dilator catheter and the locking handle are dimensionally designed to operate together each of the support catheter, the dilator and the locking handle could be used individually.

Furthermore, the aforementioned catheter system for use in a method of treating a chronic total occlusion is described.

Further examples of the present disclosure are provided below:

A. A crossing catheter system for crossing chronic total occlusion including or consisting of a support catheter having a distal support catheter end, a proximal support catheter end and a support catheter shaft extending between the support catheter distal end and the support catheter proximal end, wherein the support catheter shaft defines a support catheter lumen capable of receiving a dilator;

a dilator having a distal dilator end, a proximal dilator end and a dilator shaft extending between the distal dilator end and the proximal dilator end, the dilator being at least partially arranged within the support catheter lumen of the support catheter, wherein the distal dilator end has a proximal segment, a distal segment and one or more intermediate segments being arranged between the proximal segment and the distal segment, wherein the proximal segment is the segment, which is connected to the dilator shaft; and wherein the distal segment has a uniform radial circumference and the proximal segment has a uniform radial circumference, and wherein the radial circumference of the distal segment is smaller than the radial circumference of the proximal segment, and wherein the radial circumference of the one or more intermediate segments gradually or non-constantly decreases from the proximal segment to the distal segment, a locking handle for locking the dilator in a defined position within the support catheter shaft wherein the locking handle is arranged at the proximal support catheter end or the support catheter shaft, and optionally at least one manifold.

B. The crossing catheter system according to example A, wherein the distal support catheter end is straight-edged or tubular shaped.

C. The crossing catheter system according to example A or example B, wherein the support catheter, preferably the support catheter shaft and/or the distal support catheter end are made of a reinforced material.

D. The crossing catheter system according to any one of the preceding examples including at least one manifold, preferably a support catheter manifold and a dilator manifold.

E. The crossing catheter system according to example D, including a support catheter manifold which is connected to the locking handle.

F. The crossing catheter system according to any one of the preceding examples, wherein the support catheter may include one or more support catheter ports, preferably situated at the support catheter manifold.

G. The crossing catheter system according to any one of the preceding examples, wherein the dilator is solid.

H. The crossing catheter system according to any one of the preceding examples, wherein the dilator includes one or more dilator lumens.

I. The crossing catheter system according to example H, wherein the dilator includes one or more dilator lumens running through the distal segment and the dilator shaft.

J. The crossing catheter system according to example G, wherein the dilator shaft is solid and one or more lumens run parallel to the dilator shaft.

K. The crossing catheter system according to example J, wherein the one or more lumens run parallel to the distal dilator end.

L. The crossing catheter system according to example J, wherein the one or more lumens run parallel to the proximal segment.

M. The crossing catheter system according to example J, wherein the one or more lumens run parallel to the proximal segment and the one or more intermediate segments.

N. The crossing catheter system according to example I, wherein the one or more lumens run parallel to the proximal segment and the one or more intermediate segments and the distal segment.

O. The crossing catheter system according to any one of the examples A to F or H to N, wherein the dilator includes a first lumen capable of receiving a guidewire and a second lumen capable receiving a fluid medium, preferably a contrast agent.

P. The crossing catheter system according to any one of the preceding examples, wherein the dilator, preferably the dilator manifold includes a dilator port for injecting fluid medium, preferably a contrast agent, into at least one of the one or more dilator lumens.

Q. The crossing catheter system according to any one of the preceding examples, wherein the distal support catheter end and/or the distal segment has rounded or blunt edges.

R. The crossing catheter system according to any one of the preceding examples, wherein the distal dilator end has only one intermediate segment being a tapered thread, preferably having blunt flanks.

S. The crossing catheter system according to any one of the preceding examples, wherein the distal segment has a higher stiffness than the proximal segment and the one or more intermediate segments.

T. The crossing catheter system according to any one of the preceding examples, wherein the distal dilator end, preferably the distal segment, and/or the distal support catheter end include a radiopaque marker or are made of a radiopaque material.

U. The crossing catheter system according to any one of the preceding examples, wherein the distal support catheter end includes a metal ring or a metal cap having an opening enabling the dilator tip to fit through the opening.

V. A method of operating a crossing catheter system according to any one of examples A to U,
   inserting the dilator into the support catheter lumen of the support catheter, and
   optionally retracting at least the proximal part of the distal dilator end into the distal support catheter end, and locking the dilator in a defined position within the support catheter lumen with the locking handle, wherein in the defined position at least the proximal segment of the distal dilator end is situated in the support catheter lumen or the distal dilator end is not is situated in the support catheter lumen,
   optionally injecting a contrast agent into at least one of the one or more dilator lumens.

W. A crossing catheter system for crossing chronic total occlusion including or consisting of
   a support catheter having a distal support catheter end, a proximal support catheter end and a support catheter shaft extending between the support catheter distal end and the support catheter proximal end, wherein the support catheter shaft defines a support catheter lumen capable of receiving a dilator;
   a dilator having a proximal dilator end, a dilator shaft being attached to the proximal dilator end and being connectable to a distal dilator end, and optionally the distal dilator end being connectable to the dilator shaft.

X. The crossing catheter system according to example W, wherein the distal dilator end includes or consists of at least one segment, preferably two or three segments.

Y. The crossing catheter system according to example W or X, wherein the distal dilator end has a proximal segment, a distal segment and optionally one or more intermediate segments being arranged between the proximal segment and the distal segment, wherein the proximal segment is the segment, which is connectable to the dilator shaft.

Z. The crossing catheter system according to any one of examples W to Y, wherein the distal segment has a uniform circumference and the proximal segment has uniform circumference, and wherein the uniform circumference of the distal segment is smaller than the uniform circumference of the proximal segment.

AA. The crossing catheter system according to any one of examples W to Z, wherein the distal dilator end has a one or more intermediate segments being arranged between the proximal segment and the distal segment.

BB. The crossing catheter system according to any one of examples W to AA, wherein the circumference of the one or more intermediate segments gradually or non-constantly decreases from the proximal segment to the distal segment.

CC. The crossing catheter system according to any one of examples W to BB, wherein the proximal segment is replaceable by another proximal segment and/or wherein the distal segment is replaceable by another distal segment and/or wherein each of the intermediate segments is replaceable by another intermediate segment.

DD. The crossing catheter system according to any one of examples W to CC, further including a locking handle for locking the dilator in a defined position within the support catheter shaft wherein the locking handle is arranged at the proximal support catheter end or the support catheter shaft and optionally including at least one manifold.

EE. The crossing catheter system according to any one of examples W to DD, wherein the distal support catheter end is straight-edged or tubular shaped.

FF. The crossing catheter system according to any one of examples W to EE, wherein the support catheter, preferably the support catheter shaft and/or the distal support port catheter end are made of a reinforced material.

GG. The crossing catheter system according to any one of examples W to FF, further including at least one manifold, preferably a support catheter manifold and a dilator manifold.

HH. The crossing catheter system according to any one of examples W to GG, including a support catheter manifold which is connected to the locking handle.

II. The crossing catheter system according to any one of examples W to HH, wherein the support catheter may include one or more support catheter ports, preferably situated at the support catheter manifold.

JJ. The crossing catheter system according to any one of examples W to II, wherein the dilator is solid or includes one or more dilator lumens, preferably a first lumen capable of receiving a guidewire and a second lumen capable receiving a fluid medium, preferably a contrast agent.

KK. The crossing catheter system according any one of examples W to JJ, wherein the dilator, preferably the dilator manifold includes a dilator port for injecting fluid medium, preferably a contrast agent, into at least one of the one or more dilator lumens.

LL. The crossing catheter system according any one of examples W to KK, wherein the distal support catheter end and/or the distal segment has rounded or blunt edges.

MM. The crossing catheter system according any one of examples W to LL, wherein the distal dilator end has only one intermediate segment being a tapered thread, preferably having blunt flanks.

NN. The crossing catheter system according any one of examples W to MM, wherein the distal segment has a higher stiffness than the proximal segment and the one or more intermediate segments.

OO. The crossing catheter system according to any one of examples W to NN, wherein the distal dilator end, preferably the distal segment, and/or the distal support catheter end include a radiopaque marker or are made of a radiopaque material.

PP. The crossing catheter system according any one of examples W to OO, wherein the distal support catheter end includes a metal ring or a metal cap having an opening enabling the dilator tip to fit through the opening.

QQ. The crossing catheter system according any one of examples W to PP, wherein the dilator is solid.

RR. The crossing catheter system according any one of examples W to PP, wherein the dilator includes one or more dilator lumens.

SS. The crossing catheter system according to example RR, wherein the dilator includes one or more dilator lumens running through the distal segment and the dilator shaft.

TT. The crossing catheter system according to example QQ, wherein the dilator shaft is solid and one or more lumens run parallel to the dilator shaft.

UU. The crossing catheter system according to example TT, wherein the one or more lumens run parallel to the distal dilator end.

VV. The crossing catheter system according to example TT, wherein the one or more lumens run parallel to the proximal segment of the distal dilator end.

WW. The crossing catheter system according to example TT, wherein the one or more lumens run parallel to the proximal segment of the distal dilator end and the one or more intermediate segments of the distal dilator end.

XX. The crossing catheter system according to example TT, wherein the one or more lumens run parallel to the proximal segment of the distal dilator end and the one or more intermediate segments of the distal dilator end and the distal segment of the distal dilator end.

YY. A distal dilator end having at least one segment and being connectable to a dilator shaft via a force fit and/or form fit connection and/or a magnetic force.

ZZ. The distal dilator end according to example YY, wherein the distal dilator end includes or consists of at least one segment, preferably two or three segments.

AAA. The distal dilator end according to example YY, wherein the distal dilator end has a proximal segment, a distal segment and optionally one or more intermediate segments being arranged between the proximal segment and the distal segment, wherein the proximal segment is the segment, which is connectable to the dilator shaft.

BBB. The distal dilator end according to example AAA, wherein the distal segment has a circumference and the proximal segment has circumference, and wherein the circumference of the distal segment is smaller than the circumference of the proximal segment.

CCC. The distal dilator end according to example AAA, wherein the distal dilator end has a one or more intermediate segments being arranged between the proximal segment and the distal segment.

DDD. The distal dilator end according to example BBB, wherein the circumference of the one or more intermediate segments gradually or non-constantly decreases from the proximal segment to the distal segment.

EEE. The distal dilator end according to example AAA, wherein the proximal segment is replaceable by another proximal segment and/or wherein the distal segment is replaceable by another distal segment and/or wherein each of the intermediate segments is replaceable by another intermediate segment.

FFF. The distal dilator end according to example AAA, wherein the distal segment has a uniform diameter or circumference.

GGG. The distal dilator end according to example CCC, wherein the proximal segment has a uniform diameter or circumference.

HHH. The distal dilator end according to example AAA, wherein the distal dilator end has only one intermediate segment being a tapered thread, preferably having blunt flanks.

FIG. 1 shows a crossing catheter system 1 including a support catheter 2, a dilator 3 with a distal dilator end 32 and a locking handle 4. The support catheter shaft 23 defines a support catheter lumen 26 capable of receiving the dilator 3. Thus, the dilator 3 is arranged within the support catheter lumen 26 of the support catheter 2. The dilator shaft and/or the support catheter shaft may be reinforced.

Figure 2:
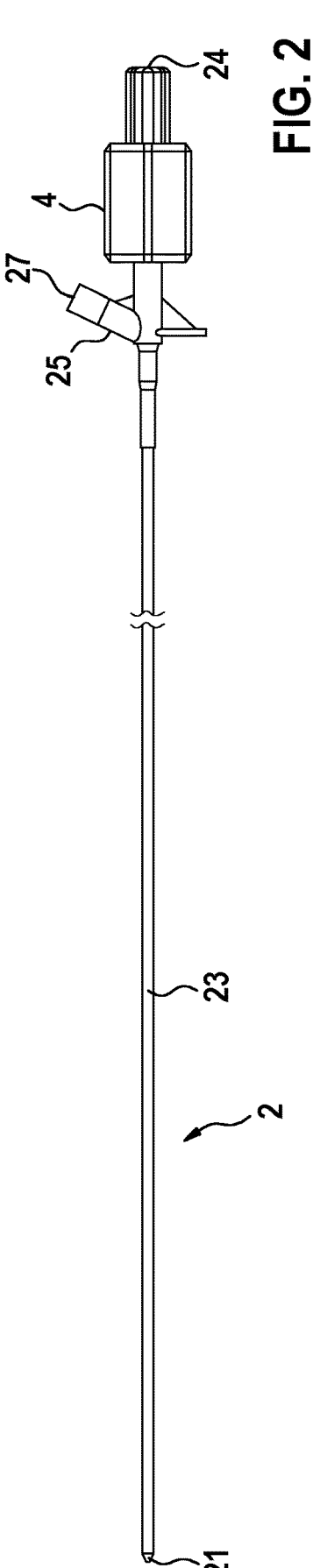
FIG. 2 shows an embodiment of a support catheter.

In FIG. 2 a support catheter 2 is shown. The support catheter 2 has a distal support catheter end 21, a proximal support catheter end 24 and a support catheter shaft 23 extending between the support catheter distal end 21 and the support catheter proximal end 24. The proximal support catheter end 24 includes a locking handle 4 or may be connected to the locking handle 4. The locking handle may have a gripping surface and an ergonomic design. The support catheter may include a manifold which is connected to the locking handle 4. The support catheter 2 may include one or more support catheter ports 27, preferably one or more port for a fluid medium, e.g. flushing port, inflation and/or deflation port. The distal support catheter end 21 is the end which is inserted into a human or animal body. The proximal outer catheter end 24 is the end, which is operated by an operator, in particular a physician.

Figure 3:
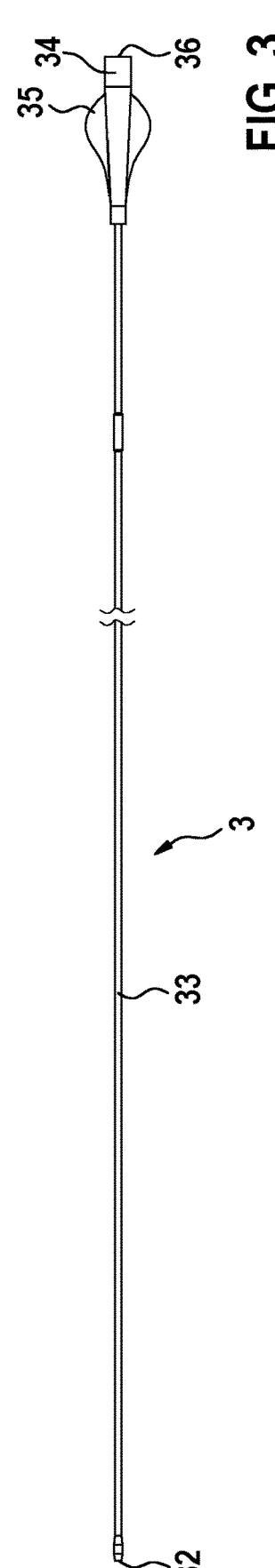
FIG. 3 shows an embodiment of a dilator.

FIG. 3 shows a dilator 3 having a distal dilator end 32, a proximal dilator end 34 and a dilator shaft 33 extending between the distal dilator end 32 and the proximal dilator end 34. The distal dilator end 32 may be a tapered dilator tip. The proximal dilator end 34 may include a dilator manifold 35. The dilator manifold can have a shape with which the operator, e.g. a physician can easily use it to manipulate the dilator. The dilator may include one or more dilator lumens (not visible). Preferably, the dilator includes a first lumen for receiving a guidewire and a second lumen for receiving a fluid medium, e.g. contrast agent. However, the dilator may have only one lumen enabling at the same time injection of a guidewire and a contrast agent. The dilator, preferably the dilator manifold 35 can include a dilator port 36 for injecting fluid medium (e.g. a contrast agent) into at least one of the dilator lumens.

Figure 4:
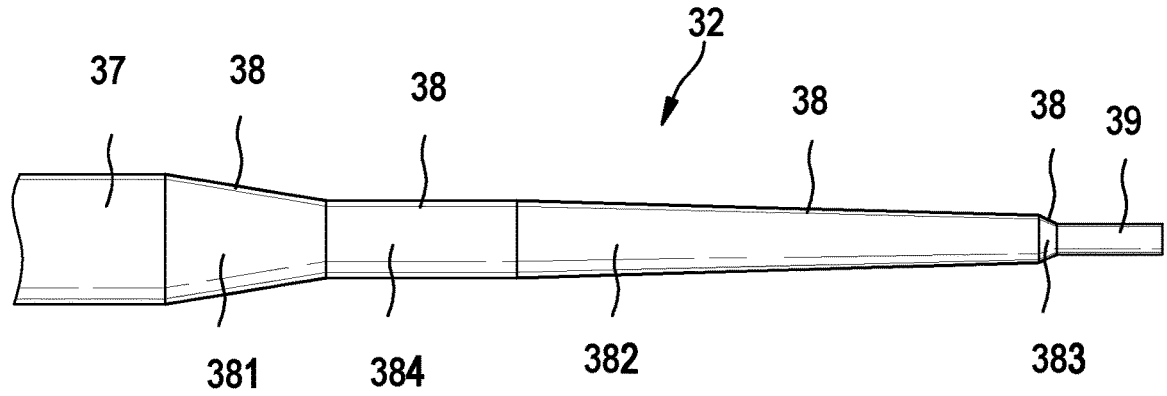
FIG. 4 shows an embodiment of a distal dilator end.

FIG. 4 shows an embodiment of a distal dilator end 32. The distal dilator end 32 has at least three different segments 37, 38, 39. The distal dilator end 32 has a proximal segment 37, a distal segment 39 and one or more intermediate segments 38 being arranged between the proximal segment 37 and the distal segment 39. The proximal dilator segment 37 is the segment, which is connected or connectable to the dilator shaft (not shown here) and the intermediate segment 38. The intermediate segment 38 is connected to the distal segment 39. The distal segment 39 is integrally formed with the distal dilator end 32. The distal segment 39 has a uniform radial circumference. The proximal segment 37 also has a uniform radial circumference. The radial circumference of the distal segment 39 is smaller than the radial circumference of the proximal segment 37. The radial circumference of the one or more intermediate segments 38 gradually or non-constantly decreases from the proximal segment 37 to the distal segment 39. The distal dilator end 32 is blunt and/or has rounded edges. Such a dilator distal end 32 enables a better pushability than a tapered tip portion as described in EP 3 322 470 B1. The distal dilator end, preferably the distal segment, is reinforced and/or includes a radiopaque marker or may be made of a radiopaque material.

The distal dilator end 32 has three or four intermediate segments 38, a first intermediate segment 381, a second intermediate segment 382, a third intermediate segment 383 and an optional fourth intermediate segment 384. The first intermediate segment 381 is adjacent to the proximal dilator end 37 and the second intermediate segment 382 (if there are three intermediate segments) or to the fourth intermediate segment 384 (if there are four intermediate segments). The optional fourth intermediate segment 384 is adjacent to the first intermediate segment 381 and the second intermediate segment 382. The second intermediate segment 382 is adjacent to the first intermediate segment 381 (if there are three intermediate segments) or to the fourth intermediate segment 384 (if there are four intermediate segments). The third intermediate segment 383 is adjacent to the second intermediate segment 382 and the distal segment 39. The proximal segment 37, the distal segment 39 and the intermediate segments 38 may be integrally formed with the dilator shaft The first intermediate segment 381 has a radial circumference which decreases with a first falling angle from the proximal dilator end 37 to the second intermediate segment 382 (if there are three intermediate segments) or to the fourth intermediate segment 384 (if there are three intermediate segments). The optional fourth intermediate segment 384 has a uniform radial circumference. The second intermediate segment 382 has a radial circumference which gradually decreases with a second falling angle from the first intermediate segment 381 (if there are three intermediate segments) to the third intermediate segment 383 or from the fourth intermediate segment 384 (if there are four intermediate segments) to the third intermediate segment 383. The third intermediate segment 383 has a radial circumference which gradually decreases with a third falling angle from the second intermediate segment 382 to the distal segment 39. The first falling angle and the third falling angle are larger than the second falling angle. The proximal segment 37, the distal segment 39 and the intermediate segments 38 have a circular cross-section, respectively (when cutting it orthogonal to the longitudinal axis of the distal dilator end).

The distal dilator end 32 may be solid or can include one or more lumens.

Figure 5:
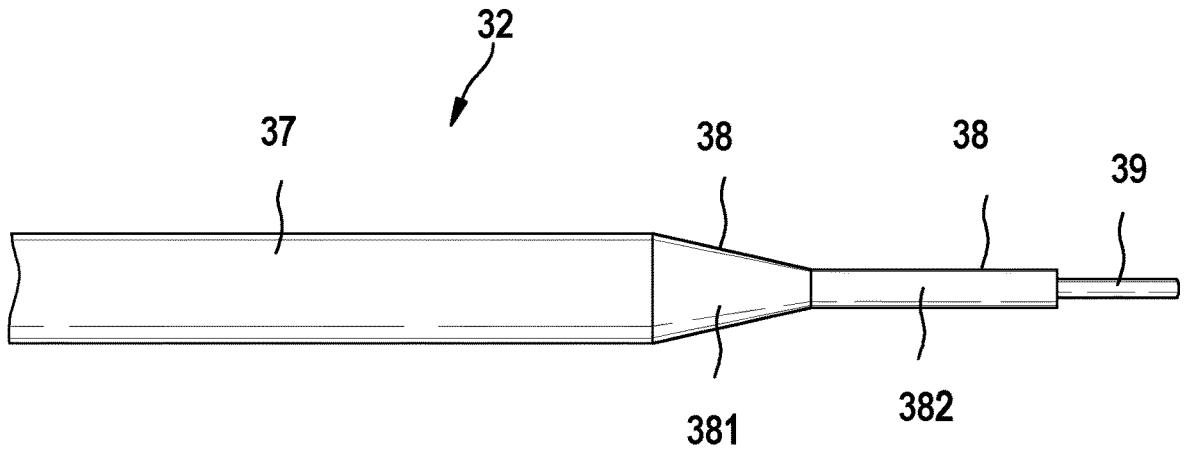
FIG. 5 shows another embodiment of a distal dilator end.

FIG. 5 shows another embodiment of a distal dilator end 32. The distal dilator end 32 has a proximal segment 37, a distal segment 39 and two intermediate segments 38 being arranged between the proximal segment 37 and the distal segment 39. The distal dilator end 32 has a first intermediate segment 381 and a second intermediate segment 382. The proximal segment 37 is connected or connectable to the dilator shaft. The first intermediate segment 381 is adjacent to the proximal dilator end 37 and the second intermediate segment 382. The second intermediate segment 382 is adjacent to the first intermediate segment 381 and the distal segment 39. The proximal segment 37, the distal segment 39 and the intermediate segments 38 may be integrally formed with the dilator shaft.

The proximal segment 37 has a uniform radial circumference. The distal segment 39 has a uniform radial circumference. The first intermediate segment 381 has a radial circumference which decreases with a first falling angle from the proximal dilator end 37 to the second intermediate segment 382. The second intermediate segment 382 has a uniform radial circumference. The radial circumference of the distal segment 39 is smaller than the radial circumference of the proximal segment 37 and the second intermediate segment 382. The proximal segment 37, the distal segment 39 and the intermediate segments 38 have a circular cross-section, respectively (when cutting it orthogonal to the longitudinal axis of the distal dilator end). The distal dilator end 32 may be blunt or may have rounded edges. Such a dilator distal end 32 enables a better pushability. The distal dilator end 32, preferably the distal segment 39, may be made of a reinforced material and/or may includes a radiopaque marker or may be made of a radiopaque material.

The tapered tip shown in FIG. 4 is much longer than the tapered tip shown in FIG. 5. The length of the distal dilator end 32 depends on the purpose of use. The distal dilator end 32 may have length of 1 mm to 5 cm.

FIGS. 6 to 32 at least partially show different distal dilator ends including at least one external thread. An external thread (similar to a screw like in FIGS. 6 to 29 or to a drill bit like in FIGS. 30 to 32) has crests, roots and flanks. The flanks are the sides that join the roots and the crests. The root is the bottom of a groove that is formed between two flanks. The crests are the heights at which the external thread is raised. The threads may have symmetrical flanks (as shown in FIGS. 11 to 14 and FIGS. 24 to 28) or the threads may have non-symmetrical flanks (as shown in FIGS. 6 to 10 and FIGS. 17 to 23). The thread may run clockwise for right-handed threads (as shown in FIGS. 6 to 13, 16 to 19, 21 to 22 and 24 to 28) or counterclockwise for left-handed threads (as shown in FIGS. 14, 20, 23 and 29). The distal dilator end may be integrally formed with the dilator shaft or may be replaceable (like a replaceable drill bit). The distal dilator end being connectable to the dilator shaft via a force fit and/or form fit connection and/or a magnetic force (e.g. a magnetic sleeve or a magnetic holder for the distal dilator end similar to a magnetic screwdriving bit holder). The distal dilator ends shown in FIGS. 6 to 32 may be solid or may include one or more lumens. The distal dilator ends shown in FIGS. 6 to 32 may be tapping or drilling dilator ends.

Figures 6, 7, 8, 9, 10:
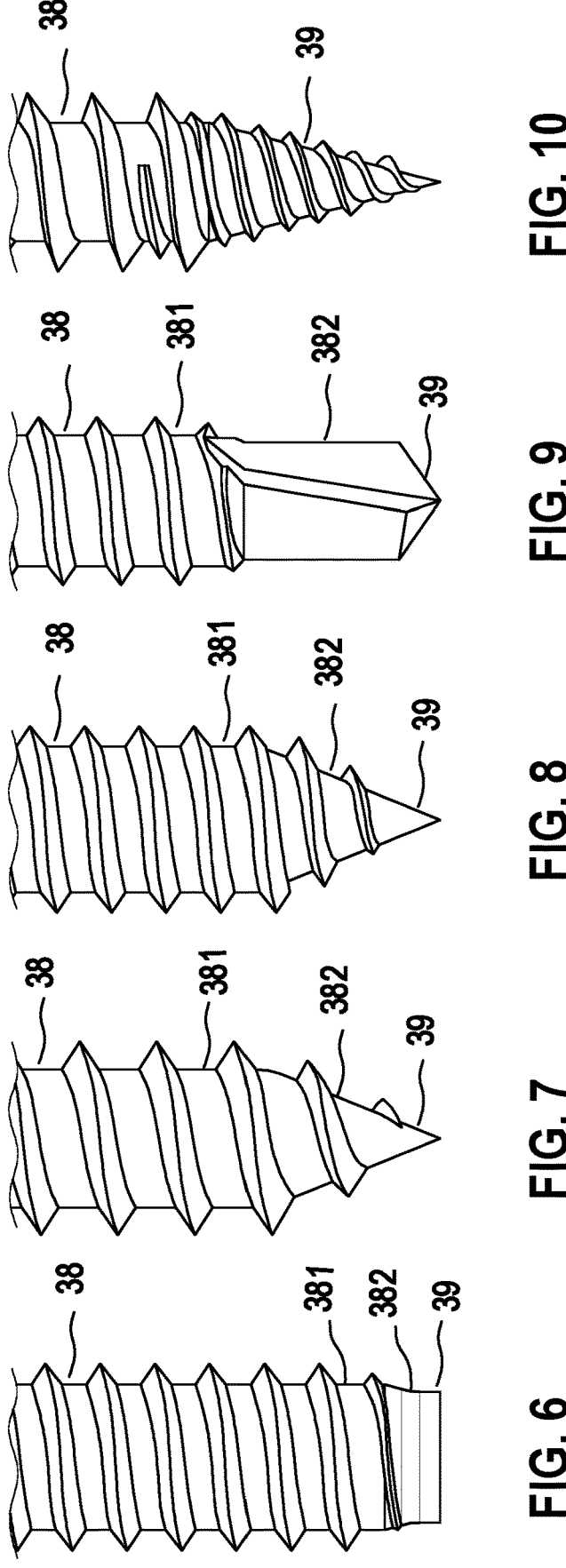
FIG. 6-29 show further embodiments of distal dilator ends being similar to screw threads.

FIG. 6 shows a distal segment 39 and a part of an intermediate segment 38 of a distal dilator end. The intermediate segment 38 includes a first intermediate segment 381 and a second intermediate segment 382. The intermediate segment 38 includes an external thread. The external thread only winds around a shaft of the first intermediate segment 381, wherein a shaft of the first intermediate segment has a uniform diameter. The second intermediate segment 382 has no thread and a tapering diameter. The distal segment 39 has a uniform radial circumference and a circular cross-section (when cutting it orthogonal to the longitudinal axis of the distal dilator end). The radial circumference of the distal segment 39 is smaller than the radial circumference of the shaft of the intermediate segment 38.

FIG. 7 shows a distal segment 39 and a part of an intermediate segment 38 of a distal dilator end. The intermediate segment 38 includes an external thread. The external thread winds around a shaft of the intermediate segment 38, wherein the intermediate segment 38 has a first intermediate segment 381 with a uniform diameter and a second intermediate 382 with a tapering diameter. The distal segment 39 has a conical shape.

FIG. 8 shows a distal segment 39 and a part of an intermediate segment 38 of a distal dilator end similar to that of FIG. 7 only having a finer thread (more threads per axial distance).

FIG. 9 shows a distal segment 39 and a part of an intermediate segment 38 of a distal dilator end. The intermediate segment 38 includes an external thread. The intermediate segment 38 includes a first intermediate segment 381 and a second intermediate segment 382. The external thread only winds around a shaft of the first intermediate segment 381, wherein a shaft of the first intermediate segment has a uniform diameter and a circular cross section (when cutting it orthogonal to the longitudinal axis of the distal dilator end). The second intermediate segment 382 has no thread and a star shape with three edges, wherein the edges being (slightly) bent around the longitudinal axis of the distal dilator end. The distal segment 39 has a tapering star shape with three edges, wherein the edges being (slightly) bent around the longitudinal axis of the distal dilator end. Thus, the distal segment 39 as well as the second intermediate segment 382 have a star like cross section (when cutting it orthogonal to the longitudinal axis of the distal dilator end).

FIG. 10 shows a distal segment 39 and a part of an intermediate segment 38 of a distal dilator end. The intermediate segment 38 as well as the distal segment each include an external thread. The distal segment 39 has a conical shape and a finer thread than the intermediate segment 38.

Figures 11, 12, 13, 14, 15, 16, 17, 18, 19, 20, 21, 22, 23:
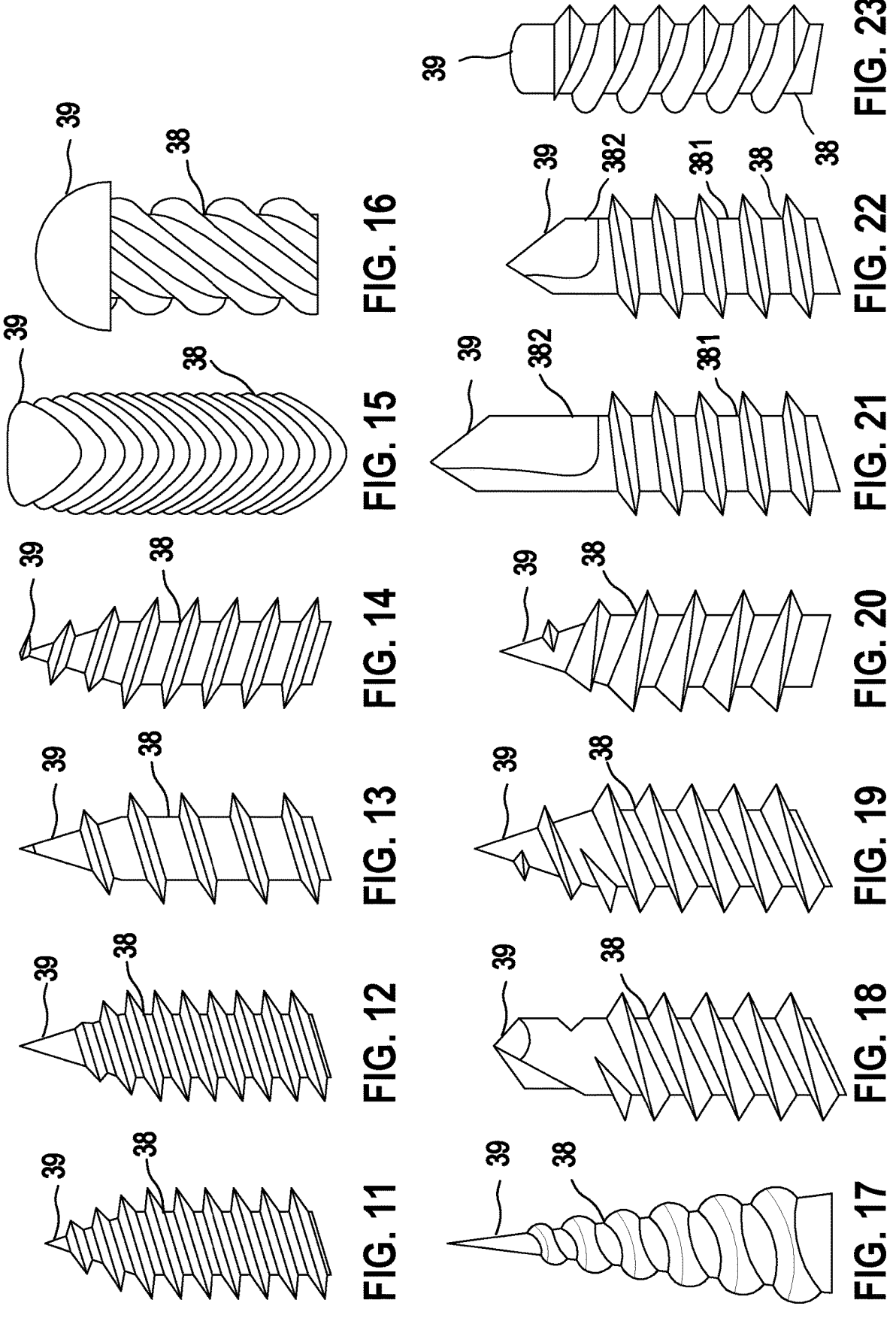

FIGS. 11 and 12 show parts of distal dilator end similar to that of FIG. 7 only having a finer thread (more threads per axial distance) and symmetrical flanks. The distal segment shown in FIG. 12 is longer than the distal segment shown in FIG. 11

FIG. 13 shows a part of a distal dilator end similar to that of FIG. 12 only having a coarser thread (fewer threads per axial distance) and symmetrical flanks.

FIG. 14 shows a part of a distal dilator end similar to that of FIG. 13 only having a finer and left-handed thread.

The root between the flanks of FIGS. 6 to 14, 18 to 22 is flat.

FIG. 15 shows a distal segment 39 and a part of an intermediate segment 38 of a distal dilator end. The intermediate segment 38 and the distal segment 39 include an external thread. The external thread winds around a shaft of the intermediate segment 38, wherein the intermediate segment 38 has a tapering circumference. The distal segment 39 has a Reuleaux triangular shape and a Reuleaux triangular shaped cross section (when cutting it orthogonal to the longitudinal axis of the distal dilator end).

FIG. 16 shows a distal segment 39 and a part of an intermediate segment 38 of a distal dilator end. The intermediate segment 38 includes an external thread. The external thread winds around a shaft of the intermediate segment 38, wherein the shaft of the intermediate segment 38 has a uniform diameter. The distal segment 39 has a hemispherical shape.

FIG. 17 shows a distal segment 39 and a part of an intermediate segment 38 of a distal dilator end. The intermediate segment 38 includes an external thread with rounded edges. The external thread winds around a shaft of the intermediate segment 38, wherein the shaft of the intermediate segment 38 has a tapering diameter. The distal segment 39 has conical shape.

FIG. 18 shows a distal segment 39 and a part of an intermediate segment 38 of a distal dilator end. The intermediate segment 38 includes an external thread which winds around a shaft of the intermediate segment 38 and wherein the shaft of the intermediate segment 38 has a uniform diameter. The distal segment 39 has a star shape with three edges, wherein the edges being parallel to the longitudinal axis of the distal dilator end. Thus, the distal segment 39 has a star shape cross section (when cutting it orthogonal to the longitudinal axis of the distal dilator end).

FIG. 19 shows a part of a distal dilator end similar to that of FIG. 13 only having non-symmetrical flanks.

FIG. 20 shows a part of a distal dilator end similar to that of FIG. 19 only having a left-handed thread.

FIG. 21 shows a distal segment 39 and a part of an intermediate segment 38 of a distal dilator end. The intermediate segment 38 includes a first intermediate segment 381 and a second intermediate segment 382, wherein the external thread only winds around a shaft of the first intermediate segment 381. The shaft of the first intermediate segment has a uniform diameter and a circular cross section (when cutting it orthogonal to the longitudinal axis of the distal dilator end). The second intermediate segment 382 has no thread and a star shape with three edges that run parallel to the longitudinal axis of the distal dilator end and a uniform circumference. The distal segment 39 has a star shape with three edges and a tapering circumference. Thus, the distal segment 39 has a star shape cross section (when cutting it orthogonal to the longitudinal axis of the distal dilator end).

FIG. 22 shows a distal segment 39 and a part of an intermediate segment 38 of a distal dilator end. The intermediate segment 38 includes a first intermediate segment 381 and a second intermediate segment 382, wherein the external thread only winds around a shaft of the first intermediate segment 381. The shaft of the first intermediate segment has a uniform diameter and a circular cross section (when cutting it orthogonal to the longitudinal axis of the distal dilator end). The second intermediate segment 382 has no thread and a uniform circumference. The second intermediate segment 382 has a cross section in the shape of a Reuleaux triangle (when cutting it orthogonal to the longitudinal axis of the distal dilator end). The distal segment having a tapering diameter and a cross section in the shape of a Reuleaux triangle (when cutting it orthogonal to the longitudinal axis of the distal dilator end).

FIG. 23 shows a distal segment 39 and a part of an intermediate segment 38 of a distal dilator end. The intermediate segment 38 includes an external thread which winds around a shaft of the intermediate segment 38, the shaft having a uniform circumference. On a first thread side the flanks have rounded edges whereas on a second thread side opposing the first thread side the flanks form spikes. The distal segment 39 has a U-shaped cross section (when cutting it parallel to the longitudinal axis of the distal dilator end).

FIGS. 24 to 28 each show a distal segment 39 and a part of an intermediate segment 38 of a distal dilator end. The intermediate segments 38 each include an external right-handed thread which winds around a shaft of the intermediate segment 38, wherein the shaft has a uniform circumference. In FIGS. 24 to 28 the flanks of the external thread form a "V". The threads in FIG. 24, 25, 27 have a smaller thread pitch and a larger helix angle than in FIGS. 26 and 28, wherein the thread pitch is the distance measured parallel to the thread axis, between corresponding points on adjacent threads. The distal segments 39 are flat and have circular cross section (when cutting it orthogonal to the longitudinal axis of the distal dilator end).

Figures 24, 25, 26, 27, 28, 29:
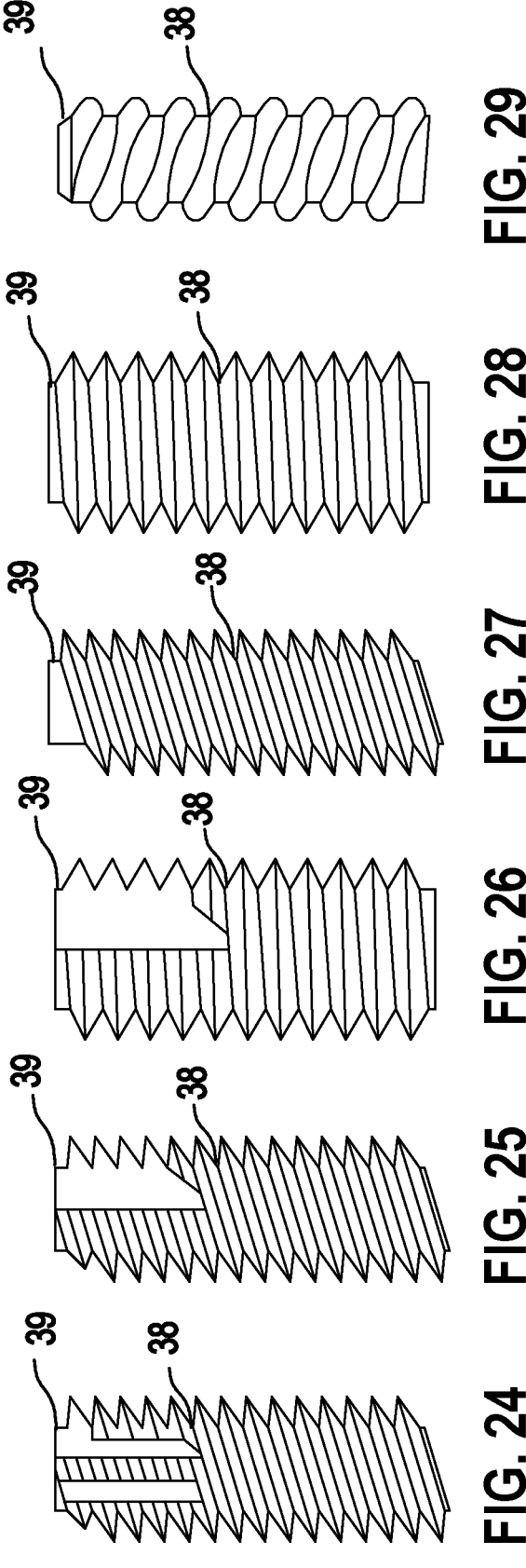

FIG. 29 shows a distal segment 39 and a part of an intermediate segment 38 of a distal dilator end. An external thread winds around a shaft of the intermediate segment 38, wherein the shaft of the intermediate segment 38 has a uniform diameter. The flanks of the thread have rounded edges. The distal segment 39 has the shape of a truncated cone with an isosceles trapezoidal cross section (when cutting it parallel to the longitudinal axis of the distal dilator end).

Figure 32:
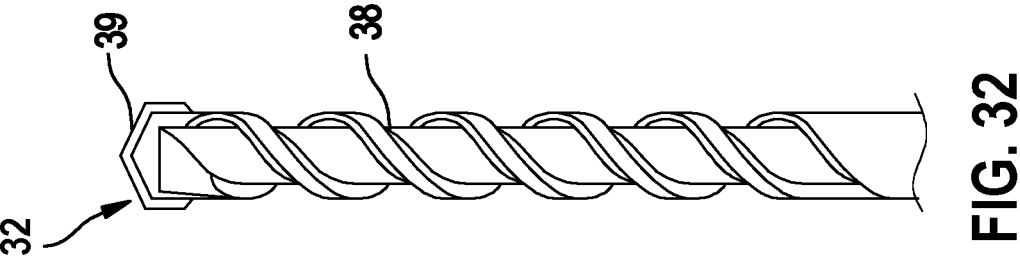
FIG. 30-32 show further embodiments of distal dilator ends being similar to drill bits.
Figure 31:
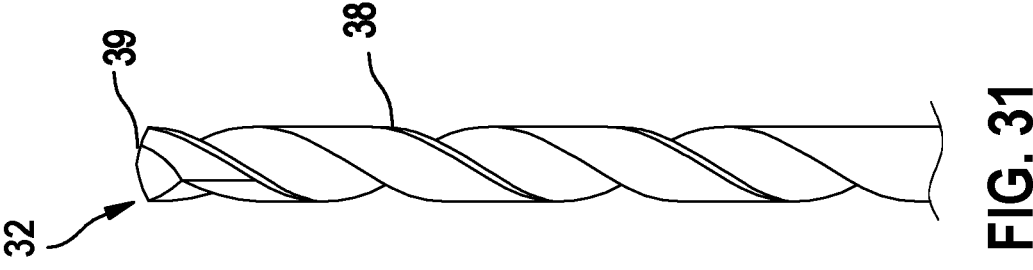
Figure 30:
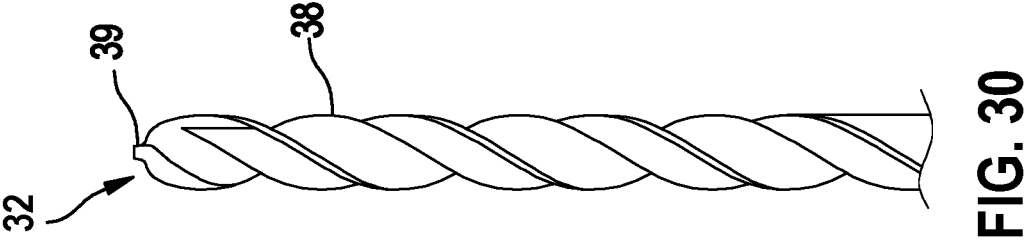

FIGS. 30 to 31 show distal dilator ends 32 being similar to twisted drill bits. Each of the intermediate segments 38 includes a cylindrical shaft with helical flutes: the flutes act like an Archimedean screw. The shafts of the intermediate segments having a uniform circumference. The distal segment 39 shown in FIG. 32 is similar to a masonry drill bit tip. The distal segment 39 of FIG. 30 has rounded cutting lips and a central spike (spur point) at its outermost distal end. The distal segment 39 of FIG. 31 is formed by the cutting lips.

LIST OF REFERENCE SIGNS

1 crossing catheter system
2 support catheter
21 distal support catheter end
23 support catheter shaft
24 proximal support catheter end
support catheter manifold
26 support catheter lumen
27 support catheter port
3 dilator
32 distal dilator end

33 dilator shaft
34 proximal dilator end
dilator manifold
36 dilator port
37 proximal segment
38 distal segment
39 intermediate segment
4 locking handle

The invention claimed is:

1. A crossing catheter system for crossing a chronic total occlusion comprising:
   a support catheter defining a lumen configured to receive a dilator, the support catheter comprising a distal support catheter end, a proximal support catheter end and a support catheter shaft extending between the support catheter distal end and the support catheter proximal end;
   a dilator at least partially arranged within the lumen, the dilator comprising a distal dilator end, a proximal dilator end and a dilator shaft extending between the distal dilator end and the proximal dilator end, wherein the distal dilator end is connected or connectable to the dilator shaft wherein the distal dilator end comprises a proximal and a distal segment, wherein the proximal segment configured to be connectable to the dilator shaft; wherein the proximal segment has a uniform radial circumference, and wherein the radial circumference of the distal segment is smaller than the radial circumference of the proximal segment; and
   a locking handle for locking the dilator in a plurality of defined positions within the lumen of the support catheter shaft, wherein the locking handle is arranged at the proximal support catheter end or the support catheter shaft, wherein the plurality of defined positions include a first position wherein distal dilator end extends distally from the distal support catheter end to perform crossing using only the dilator and second position wherein the distal dilator end is locked within the distal support catheter end to perform crossing with the combined column strength of the support catheter and the dilator with increased pushability compared to the first position.

2. The crossing catheter system according to according to claim 1, wherein the distal dilator end comprises one or more intermediate segments being arranged between the proximal segment and the distal segment, and wherein the radial circumference of the one or more intermediate segments gradually or non-constantly decreases from the proximal segment to the distal segment.

3. The crossing catheter system according to claim 1, wherein the distal dilator end is connectable to a dilator shaft via a force fit, a form fit, and/or a magnetic force.

4. The crossing catheter system according to claim 1, wherein the distal support catheter end is straight-edged, tubular shaped or rounded.

5. The crossing catheter system according to claim 1, wherein one or more of the support catheter, the support catheter shaft, and the distal support catheter end are made of a reinforced material.

6. The crossing catheter system according to claim 1, wherein the distal dilator end comprises only one intermediate segment comprising a tapered thread.

7. The crossing catheter system according to claim 1, wherein the distal segment has a higher stiffness than the proximal segment.

8. The crossing catheter system according to claim 1, wherein one or both of the distal segment and the distal support catheter end comprise a radiopaque marker or are made of a radiopaque material.

9. The crossing catheter system according to claim 1, wherein the distal support catheter end comprises a metal ring or a metal cap having an opening through which the dilator tip can fit through.

10. The crossing catheter system according to claim 1, comprising at least one manifold.

11. The crossing catheter system according to claim 10 comprising a support catheter manifold connected to the locking handle.

12. The crossing catheter system according to claim 1, wherein the support catheter comprises one or more support catheter ports.

13. The crossing catheter system according to claim 1, wherein the dilator comprises one or more dilator lumens.

14. The crossing catheter system according to claim 1, wherein the dilator is solid or the dilator shaft is solid, and wherein one or more lumens run parallel to the dilator shaft, one or more lumens run parallel to the distal dilator end, one or more lumens run parallel to the proximal segment of the distal dilator end and one or more intermediate segments of the distal dilator end, one or more lumens run parallel to the proximal segment of the distal dilator end and the one or more intermediate segments of the distal dilator end and the distal segment of the distal dilator end, or one or more dilator lumens run through the distal segment and the dilator shaft.

15. The crossing catheter system according to claim 1, wherein the dilator comprises a first dilator lumen configured to receive a guidewire and a second dilator lumen configured to receive a fluid medium.

16. The crossing catheter system according claim 15, wherein the dilator comprises a dilator port for injecting fluid medium into at least one of the first and second dilator lumens.

17. The crossing catheter system according to claim 1, wherein one or both of the support catheter and the locking handle comprise a hemostatic valve with a lockable seal.

18. The crossing catheter system according to according to claim 1, wherein the locking handle is configured to conduct penetration, pushing or advancing of the dilator during crossing.

19. A crossing catheter system for crossing a chronic total occlusion comprising:

a support catheter defining a lumen configured to receive a dilator, the support catheter comprising a distal support catheter end, a proximal support catheter end and a support catheter shaft extending between the support catheter distal end and the support catheter proximal end;

a dilator at least partially arranged within the lumen, the dilator comprising a distal dilator end, a proximal dilator end and a dilator shaft extending between the distal dilator end and the proximal dilator end, wherein the distal dilator end is connected or connectable to the dilator shaft wherein the distal dilator end comprises a proximal and a distal segment, wherein the proximal segment configured to be connectable to the dilator shaft; wherein the proximal segment has a uniform radial circumference, and wherein the radial circumference of the distal segment is smaller than the radial circumference of the proximal segment; and a locking handle for locking the dilator in a defined position within the lumen, wherein the locking handle is arranged at the proximal support catheter end or the support catheter shaft, wherein the distal segment has a uniform radial circumference along an entire length of the distal segment, is sharp or comprises sharp edges.

20. The crossing catheter system according to claim 19, wherein the proximal segment is connected to the dilator shaft.

21. The crossing catheter system according to claim 20, wherein one or more of the proximal segment, the distal segment, and the one or more intermediate segments is configured to be replaceable.

* * * * *